(12) United States Patent
Fujii et al.

(10) Patent No.: US 11,186,860 B2
(45) Date of Patent: Nov. 30, 2021

(54) MICROCHAMBER ARRAY DEVICE AND METHOD OF ANALYZING INSPECTION OBJECT USING SAME

(71) Applicant: THE FOUNDATION FOR THE PROMOTION OF INDUSTRIAL SCIENCE, Tokyo (JP)

(72) Inventors: Teruo Fujii, Tokyo (JP); Soo Hyeon Kim, Tokyo (JP); Ken Ogata, Tokyo (JP)

(73) Assignee: THE FOUNDATION FOR THE PROMOTION OF INDUSTRIAL SCIENCE, Tokyo (JP)

( * ) Notice: Subject to any disclaimer, the term of this patent is extended or adjusted under 35 U.S.C. 154(b) by 446 days.

(21) Appl. No.: 15/778,319

(22) PCT Filed: Nov. 24, 2016

(86) PCT No.: PCT/JP2016/084705
§ 371 (c)(1),
(2) Date: May 23, 2018

(87) PCT Pub. No.: WO2017/090640
PCT Pub. Date: Jun. 1, 2017

(65) Prior Publication Data
US 2019/0249220 A1    Aug. 15, 2019

(30) Foreign Application Priority Data

Nov. 25, 2015    (JP) .............................. JP2015-229660

(51) Int. Cl.
*C12Q 1/68*    (2018.01)
*C12Q 1/24*    (2006.01)
(Continued)

(52) U.S. Cl.
CPC ................. *C12Q 1/24* (2013.01); *C12M 1/00* (2013.01); *C12M 23/16* (2013.01); *C12M 33/00* (2013.01);
(Continued)

(58) Field of Classification Search
None
See application file for complete search history.

(56) References Cited

U.S. PATENT DOCUMENTS 9,314,764 B2    4/2016    Hess et al.
9,968,903 B2    5/2018    Hess et al.
(Continued)

FOREIGN PATENT DOCUMENTS

JP    2009_504161 A    2/2009
JP    2012_529643 A    11/2012
(Continued)

OTHER PUBLICATIONS

Merriam-Webster, definition effacing, available athttps://www.merriam-webster.com/dictionary/facing, accessed Apr. 27, 2020.*
(Continued)

*Primary Examiner* — Aaron A Priest
(74) *Attorney, Agent, or Firm* — Bacon & Thomas, PLLC

(57) ABSTRACT

A microchamber array device having built-in reaction microchambers, in which the dilution ratio can be greatly increased at the same time as dramatically raising cell recovery efficiency, and an inspection object analysis method using said device are provided. This microchamber array device is provided with: a microchamber array 1 for cell capture by electrophoresis comprising an arrangement of a substrate 2, electrodes 3 and photoresists 4; and a reaction microchamber array 6 which is separated from the capture microchamber array 1, and which is formed from reaction microchamber 8 comprising micro channels 7

(Continued)

arranged so as to be opposite of the aforementioned microchamber array 1.

4 Claims, 12 Drawing Sheets

(51) Int. Cl.
| | | |
|---|---|---|
| *G01N 37/00* | (2006.01) | |
| *C12Q 1/02* | (2006.01) | |
| *C12M 1/00* | (2006.01) | |
| *C12M 3/06* | (2006.01) | |
| *C12M 1/26* | (2006.01) | |
| *C12Q 1/6806* | (2018.01) | |

(52) U.S. Cl.
CPC .............. *C12M 47/04* (2013.01); *C12Q 1/02* (2013.01); *C12Q 1/6806* (2013.01); *G01N 37/00* (2013.01)

(56) References Cited

U.S. PATENT DOCUMENTS

2012/0156675 A1    6/2012  Lueerssen et al.
2012/0277114 A1 *  11/2012  Duffy .............. G01N 33/54313
                                                            506/9

FOREIGN PATENT DOCUMENTS

| WO | WO2012/020711 A1 | 2/2012 | |
| WO | WO-2012020711 A1 * | 2/2012 | ........ B01L 3/502761 |
| WO | WO2014/144822 A2 | 9/2014 | |
| WO | WO-2014144822 A2 * | 9/2014 | .......... B01J 19/0046 |

OTHER PUBLICATIONS

Merriam-Webster, definition of correspond, available at https://www.merriam-webster.com/dictionary/correspond, accessed Apr. 27, 2020.*
Eglish translation of WO2012020711A1.*
International Search Report dated Feb. 21, 2017.
Ken Ogata et al; Electro Active Microwell Array 1P30; 2015 The Society for Chemistry and Micro-Nano Systems CHEMINAS; Nov. 26, 2015: p. 34.
English Translation of International Preliminary Report dated May 31, 2018.

* cited by examiner

F I G. 9
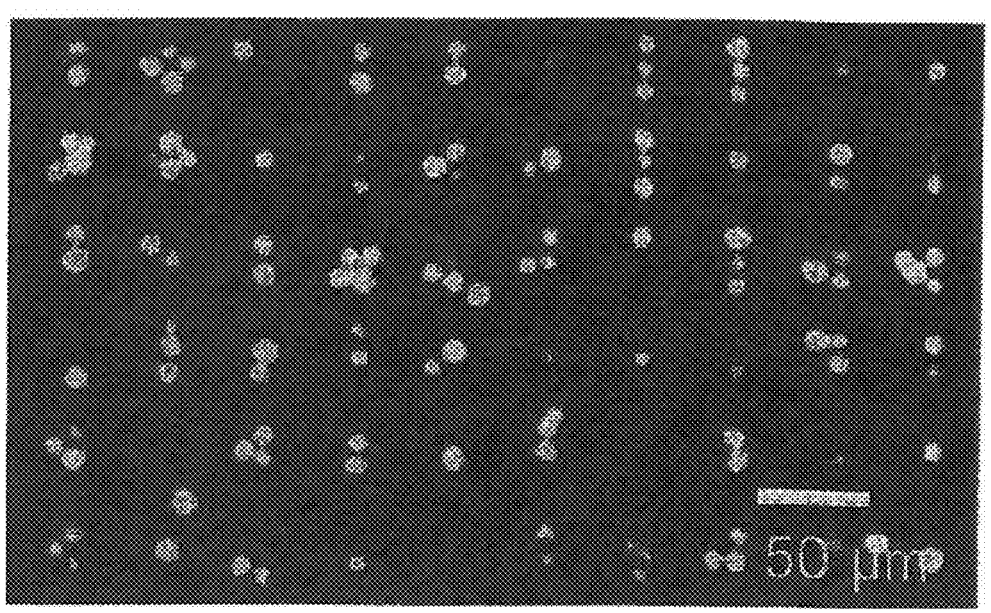

MICROCHAMBER ARRAY DEVICE AND METHOD OF ANALYZING INSPECTION OBJECT USING SAME

TECHNICAL FIELD

The present invention relates to a microchamber array device and a method of analyzing inspection object using same.

BACKGROUND ART

In recent years, researches on analysis of amount of gene expression per cell unit have been conducted, because it is indicated that gene expressions in individual cells in a cell population widely vary. And also, it is urgently required to conduct simultaneous gene expression analysis at the single-coil level in the cell population. For conducting gene expression analysis of cells, reverse transcription polymerase chain reaction (RT-PCR) is widely used.

CITATION LIST

Patent Literature

PTL-1: JP2012-34641 A1
PTL-2: JP2004-535176 A1

Non-Patent Literature

NPL-1: Soo Hyeon Kim et al., "High-efficiency rare cell trapping at the single cell level using electroactive microwell array", Proceedings of the 6th International Symposium on Microchemistry and Microsystems (ISMM), pp. 206-207, July 2014
NPL-2: Soo Hyeon Kim et al., "Highly efficient single cell arraying by integrating acoustophoretic cell pre-concentration and dielectrophoretic cell trapping", Lab on a Chip, October 2015
NPL-3: Soo Hyeon Kim et al., "Development of electroactive microwell array for rare cell analysis", the 30th Chemistry and Micro-Nano System Society, October, 2014
NPL-4: Soo Hyeon Kim et al, "Single cell analysis of rare cell using electroactive double-well array", Collected papers of academic lectures at autumn festival of 2015 of the Japan Society for Precision Engineering, pp. 783-784, August 2015

SUMMARY OF INVENTION

Problems to be Solved by Invention

However, it is necessary to dilute (1000 or more times) intracellular substances discharged from a cell for conducting gene expression analysis of a single cell using RT-PCR after crushing the single cell confined in a closed space (a microchamber). Because the intracellular substances inhibit RT-PCR.

FIG. 8 is a schematic view showing a microchamber with an enlarged diameter. FIG. 9 is a view showing a problem caused by enlarging a diameter of microchamber. FIG. 10 is a schematic view showing a microchamber with a raised height FIG. 11 is a view showing a problem caused by raising a height of microchamber. FIG. 12 is a view showing a result of simulating an electric field.

In a structure of the microchamber array device described in PTL-1, when the diameter of the microchamber is enlarged as shown in FIG. 8, two or more cells would enter one chamber, as shown in FIG. 9, and the single cell analysis would be difficult. In the same structure, when the height of the microchamber is raised as shown in FIG. 10, the recovery rate (cell recovery efficiency) would deteriorate very much, as shown in FIG. 11. Because the vector of electric field intensity gradient ($\nabla E_e^2$) points inward as shewn in FIG. 12, the intensity weakens as the distance from the electrode becomes far (as the height of the microchamber raises), and capturing cells becomes difficult by the invention using dielectrophoretic force described in PTL-1.

In a device without any channel as described in PTL-2, it would be difficult to improve the recovery efficiency by pouring cell suspension.

Thus, although improving the recovery efficiency is required for the efficient single cell analysis, there is a problem that plural cells are unable to be captured or cells are unable to be captured using dielectrophoretic force when the microchamber is enlarged for raising dilution rate.

An object of the present invention is, considering the above-mentioned situation, to provide a microchamber array device and a method of analyzing inspection object using same, which can improve the cell recovery efficiency very much as well as raise the dilution rate.

Solution to Problems

For Achieving the Object:

[1] A microchamber array device, comprising: a cell capturing microchamber array including a cell capturing microchamber made of a substrate, an electrode and a photoresist, the cell capturing microchamber capturing a cell by dielectrophoresis; and a reaction microchamber array including a reaction microchamber made of a micro channel, the reaction microchamber array being made separately from the cell capturing microchamber array and being placed opposing to the cell capturing microchamber array.

[2] The microchamber array device according to wherein positions of the cell capturing microchamber and the reaction microchamber correspond to each other, and the cell capturing microchamber and the reaction microchamber are able to form a closed microchamber at a time of analysis.

[3] The microchamber array device according to [1] or [2], wherein a cell suspension and a solution for analysis are introducible into a space between the cell capturing microchamber array and the reaction microchamber array.

[4] The microchamber array device according to any one of [1]-[3], wherein the reaction microchamber is 20 µm-200 µm in diameter, and 10 µm-1000 µm in height.

[5] The microchamber array device according to any one of [1]-[4], wherein the cell is captured in the cell capturing microchamber one by one, dilution rate of the cell at a time of analysis can be raised by enlarging a volume of the reaction microchamber and a cell recovery efficiency of 90% or more can be achieved.

[6] A method of analyzing inspection object using a microchamber array device, comprising: introducing a cell suspension into a space between a cell capturing microchamber array and a reaction microchamber array; capturing a cell by dielectrophoresis; exchanging reagents by introducing analysis solution; sealing the captured cell with the cell capturing microchamber array and the reaction microchamber array; and analyzing the cell.

Effects of Invention

According to the present invention, each of cells is captured one by one in each of chambers and a high recovery efficiency can be maintained even when the height of chamber raises. For example, it is possible to improve the cell recovery efficiency very much (90% or more) as well as to raise the dilution rate (1000 times or more).

BRIEF DESCRIPTION OF DRAWINGS

FIG. 9 is a view showing a problem caused by enlarging a diameter of microchamber.

DESCRIPTION OF EMBODIMENTS

A microchamber array device of the present invention comprising: a cell capturing microchamber array including a cell capturing microchamber made of a substrate, an electrode and a photoresist, the cell capturing microchamber capturing a cell by dielectrophoresis; and a reaction microchamber array including a reaction microchamber made of a micro channel, the reaction microchamber array being made separately from the cell capturing microchamber array and being placed opposing to the cell capturing microchamber array.

And a method of analyzing inspection object using a microchamber array device, comprising: introducing a cell suspension into a space between a cell capturing microchamber array and a reaction microchamber array; capturing a cell by dielectrophoresis; exchanging reagents by introducing analysis solution; sealing the captured cell with the cell capturing microchamber array and the reaction microchamber array; and analyzing the cell.

Embodiment

An embodiment of the present invention will next be explained in detail.

Figure 1:
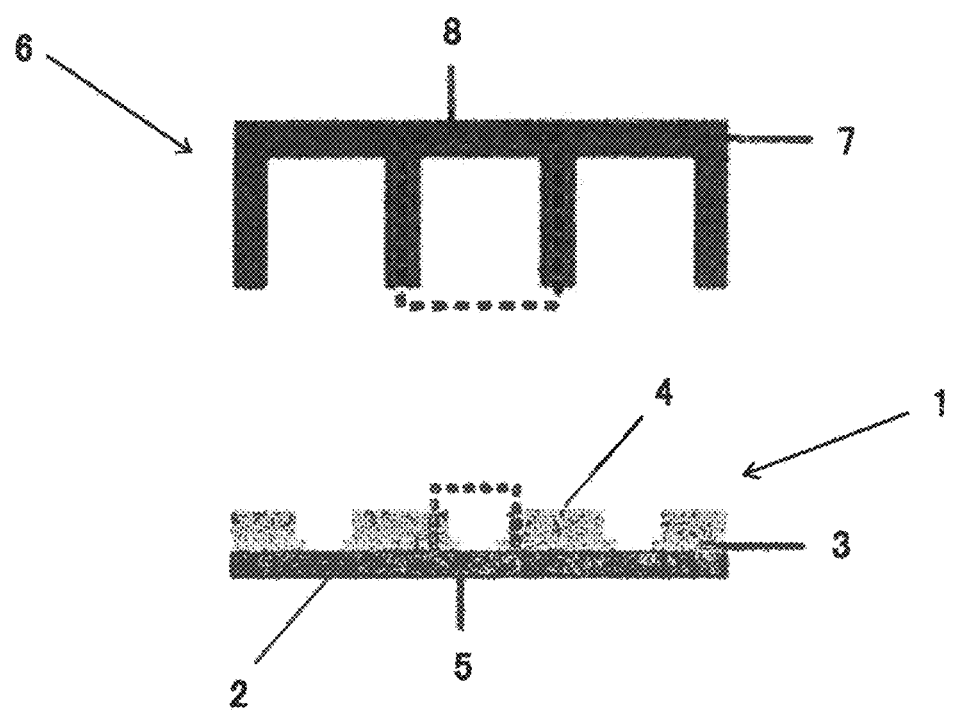
FIG. 1 is a schematic view showing a microchamber array device according to the embodiment of the present invention.
Figure 2:
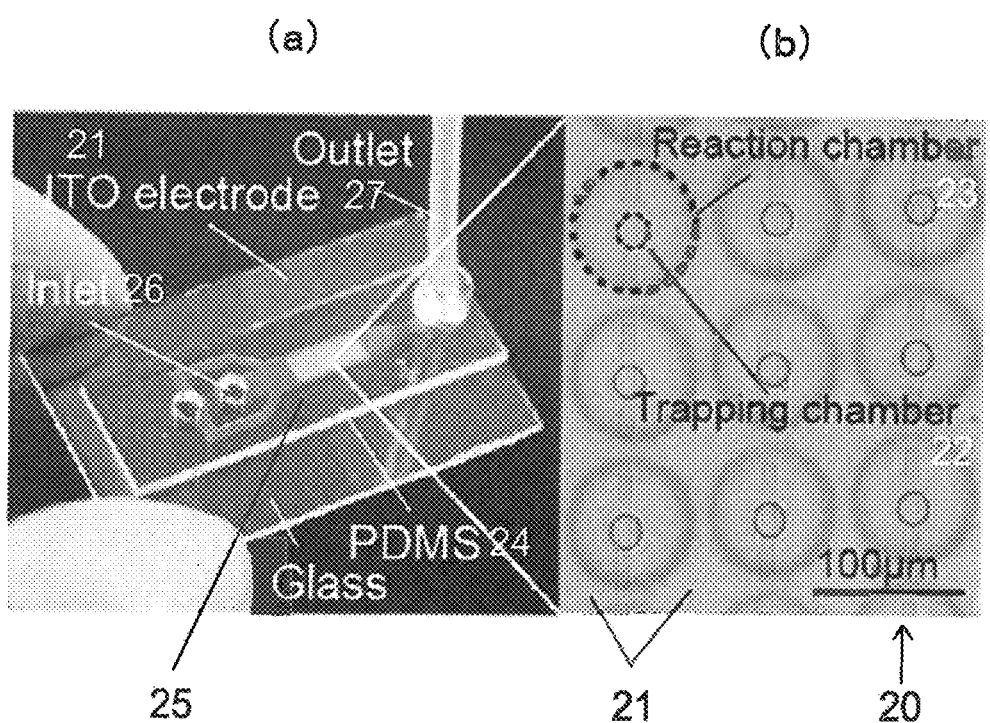
FIG. 2 is a set of photographs showing a microchamber array device according to the embodiment of the present invention.

FIG. 1 is a schematic view showing a microchamber array device according to the embodiment of the present invention. FIG. 2 is a set of photographs showing a microchamber array device according to the embodiment of the present invention. In FIG. 2, (a) is a photograph showing a perspective view of a microchamber array device and (b) is a photograph showing an enlarged plan view of an array portion of the microchamber array device shown in (a).

First, an outline of a microchamber array device of the present invention will be described with reference to FIG. 1.

The microchamber array device of the present invention comprises, as a lower structure, a cell capturing microchamber array 1 and, as an upper structure, a reaction microchamber array 6. The upper and lower structures are made separately and are placed as opposing each other.

In the cell capturing microchamber array 1, plural cell capturing microchambers 5 made of a substrate 2, electrodes 3 and photoresists 4 are formed as an array. In the reaction microchamber array 6 consisting of micro channels 7, plural reaction microchambers 8, each of which has a hollow shape and is placed corresponding to the cell capturing microchamber 5, are formed as an array. A flow path will be formed between the cell capturing microchamber array 1 and the reaction microchamber array 6 so as to effectively capture cells in the device. Cell suspension will be introduced into the flow path and cells will be captured in the cell capturing microchambers 5 by dielectrophoresis. The cell capturing microchamber array 1 and the reaction microchamber array 6 are placed in such a way that each of the cell capturing microchambers 5 and each of the reaction microchambers 8 will form a closed microchamber when the cell capturing microchamber array 1 and the reaction microchamber array 6 contact each other. Each of captured cells will be able to be analyzed in the closed microchamber.

Thus, with making the cell capturing microchamber and the reaction microchamber separately, it will be possible to achieve an improved recovery efficiency of cells by dielectrophoresis and a high (1000 times or more) dilution rate by forming closed microchambers in case of analysis.

In this description, the "recovery efficiency" of cell refers to a rate of the captured cells to the flowing ones on the cell capturing microchamber array 1. For example, in case that 95 cells are captured from 1000 flowing cells, the cell recovery efficiency is 9.5%. On the other hand, the "capture efficiency" of cell in PTL-1 refers to a rate of microchamber occupancy by cells in a microchamber array. For example, in case that 96 microchambers captured cells from 1000 cells flowing on the microchamber array of 100 microchambers, the cell capture efficiency of microchamber array is 95%. Thus, it is noted that the definitions of these two efficiencies are different.

Next will be described structures of parts of the microchamber array device of the present invention, with reference to FIG. 2.

In FIG. 2, a reference numeral 20 designates a substrate, a reference numeral 21 designates an electrode, a reference numeral 22 designates a trapping microchamber or a cell capturing microchamber, a reference numeral 23 designates a reaction microchamber, a reference numeral 24 designates a micro channel, a reference numeral 25 designates an array portion, a reference numeral 26 designates an inlet and a reference numeral 27 designates an outlet.

The substrate 20 is a glass substrate and others, and the electrode 21 is formed on the substrate 20. The electrode 21 is an ITO electrode and others, and comb-like shaped ITO electrodes may be arranged in a way to engage each other. The diameter of the cell capturing microchamber 22, which is formed in a way to cross the electrode 21, is approximately made in a size of a cell. And the height is made low (for example, 4 µm) so as to increase the cell capture efficiency. The cell suspension containing the cells as analysis objects and a solution for analysis are introduced into the microchamber array device from the inlet 26, flow through the flow path between the cell capturing microchamber array 1 and the reaction microchamber array 6 and are exhausted from the outlet 27. The array portion 25 shown in FIG. 2(b) has the same structure as shewn in FIG. 1, and the micro channel 24 is made of PDMS.

Thus, by making the diameter of the cell capturing microchamber 22 approximately in a size of a cell, two or more cells are not captured in one microchamber. By closing the flow path after capturing cells, microchambers, closed with the cell capturing microchambers 22 and the reaction mien chambers 23, can be formed and the cells can be compartmentalized.

Figure 3:
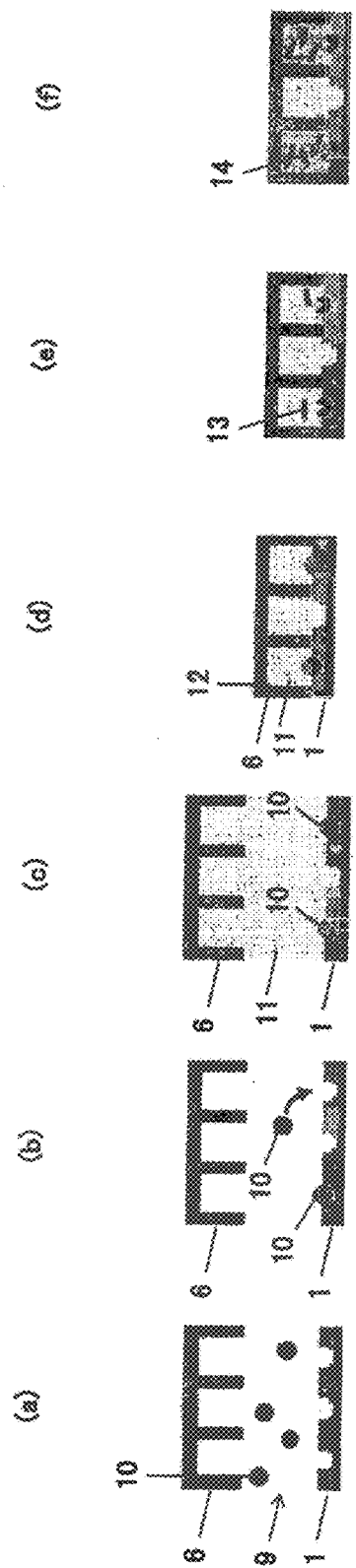
FIG. 3 is a set of schematic views illustrating analyzing steps of inspection object using a microchamber array device according to the embodiment of the present invention.

FIG. 3 is a set of schematic views illustrating analyzing steps of inspection object using a microchamber array device according to the embodiment of the present invention. Next will be a case that RT-PCR is used for analysis.

In FIG. 3, a reference numeral 9 designates a cell suspension, a reference numeral 10 designates a cell as an inspection object, a reference numeral 11 designates an analysis solution, a reference numeral 12 designates a closed microchamber, a reference numeral 13 designates an intracellular substance, a reference numeral 14 designates an amplified DNA. Some of the reference numerals designating the same parts as in FIG. 1 are omitted but referred in the following description.

First as shown in FIG. 3(a), the cell suspension 9 is introduced between the cell capturing microchamber array 1 and the reaction microchamber array 6.

Next, as shown in FIG. 3(b), by dielectrophoresis using the electrodes 3, the cells 10 are captured in the cell rapturing microchambers 5 of the cell capturing microchamber array 1.

Next, as shown in FIG. 3(c), the analysis solution 11 is introduced so as to exchange reagents.

Next, as shown in FIG. 3(d), the flow path between the cell capturing microchamber 1 and the reaction microchamber array 6 is closed, the cell capturing microchambers 5 and the reaction microchambers 8 contact each other so as to form the closed microchambers 12, and the captured cells 10 are sealed.

Next, as shown in FIG. 3(e), high voltage is applied to the electrodes in the closed microchambers 12 so as to crash the captured cells 10 by electroporation. Thereby, the intracellular substances 13 are discharged in the closed microchambers 12 and diluted with the analysis solution 11.

Next, as shown in FIG. 3(f), the analysis is conducted in the closed microchambers 12. For example, in a case of RT-PCR, the analysis of amplified DNA 14 is conducted. Inhibition of RT-PCR by the intracellular substances 13 can be prevented by making the volume of the reaction microchamber big enough to dilute the intracellular substances 13 a thousand times as much or more.

As described above, according to the microchamber array device of the present invention, the high cell recovery efficiency can be achieved because the cell capturing microchamber array 1 captures the cells in a state of separation from the reaction microchamber array 6, and after capturing cells, the analysis under the condition of high dilution rate (1000 times or more) can be conducted because the closed microchambers 12 are formed of the reaction microchambers 8 and the cell capturing microchambers 5 filled with the analysis solution.

Figure 4:
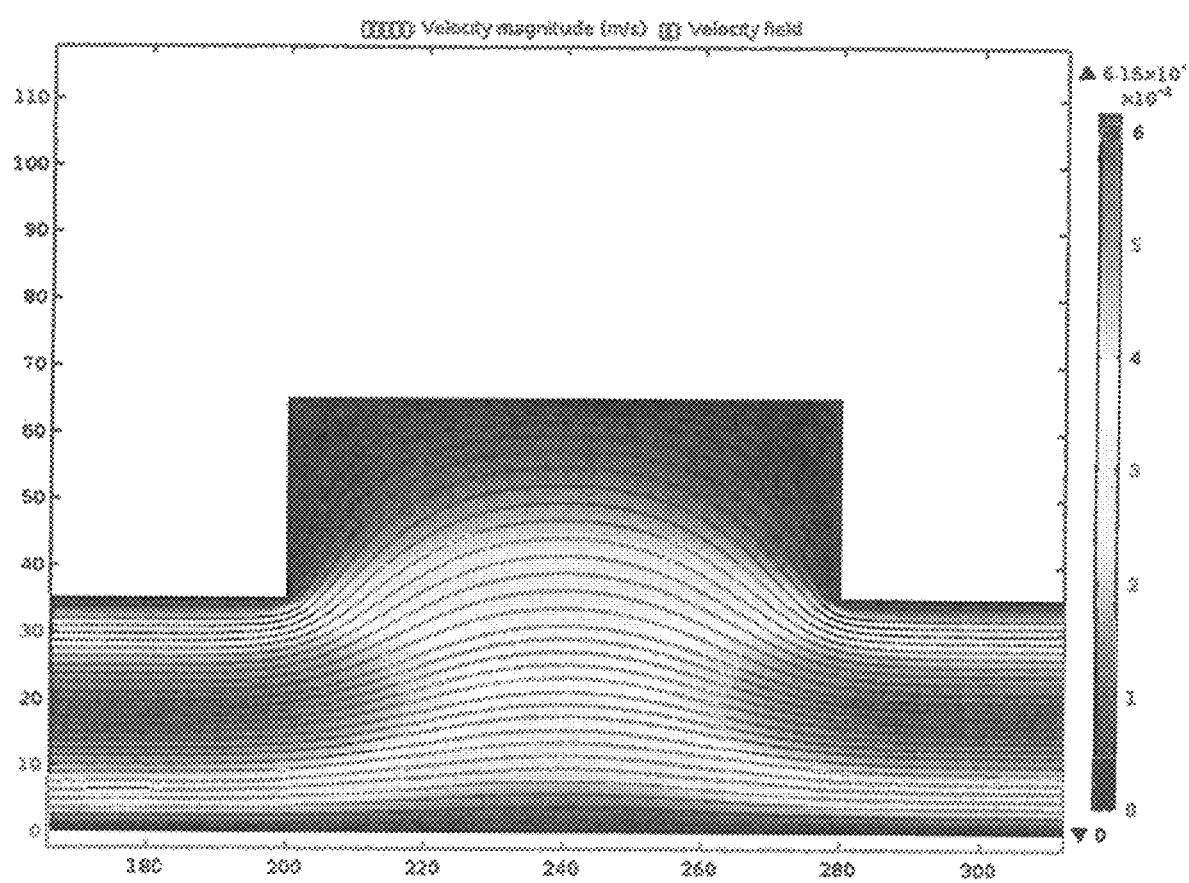
FIG. 4 is a diagram illustrating flow velocities and flow lines in a reaction microchamber 30 μm in height according to the embodiment of the present invention.
Figure 5:
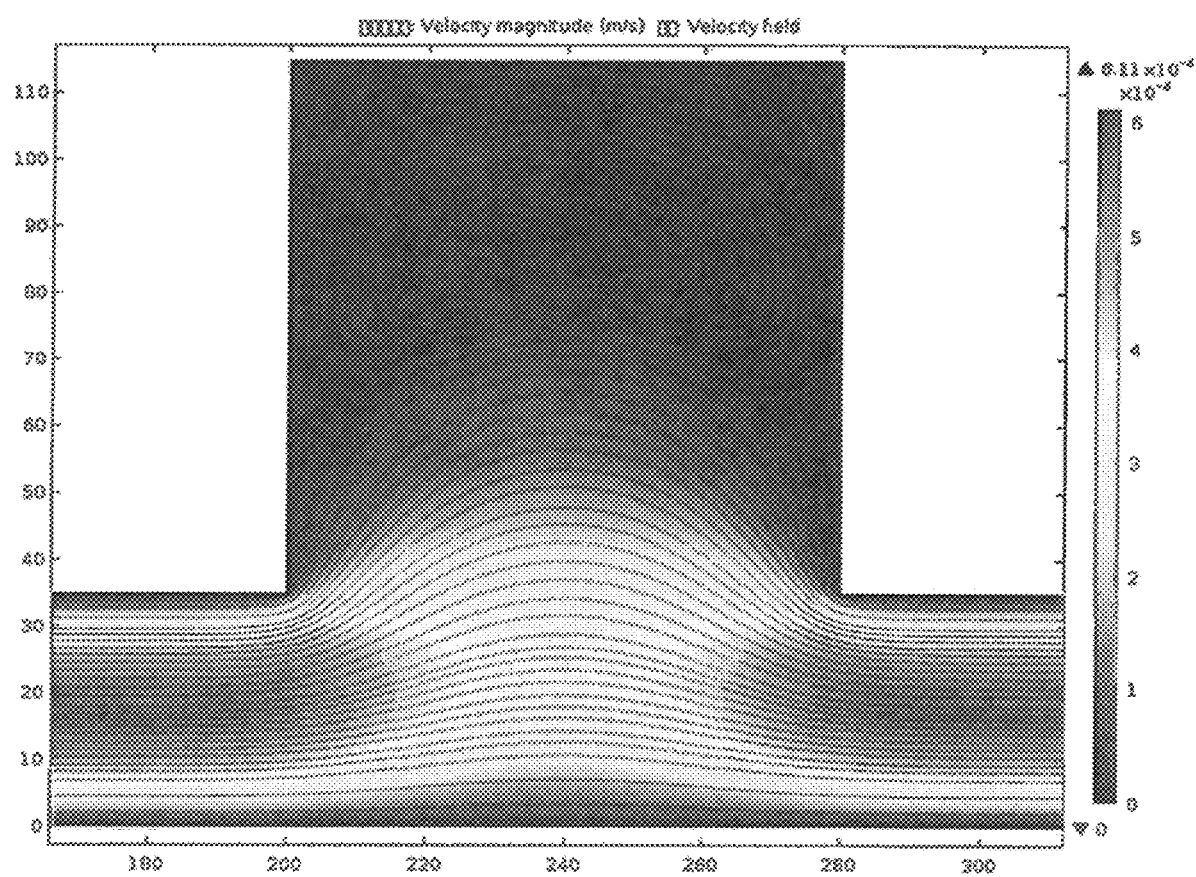
FIG. 5 is a diagram illustrating flow velocities and flow lines in the reaction microchamber 80 μm in height according to the embodiment of the present invention.
Figure 6:
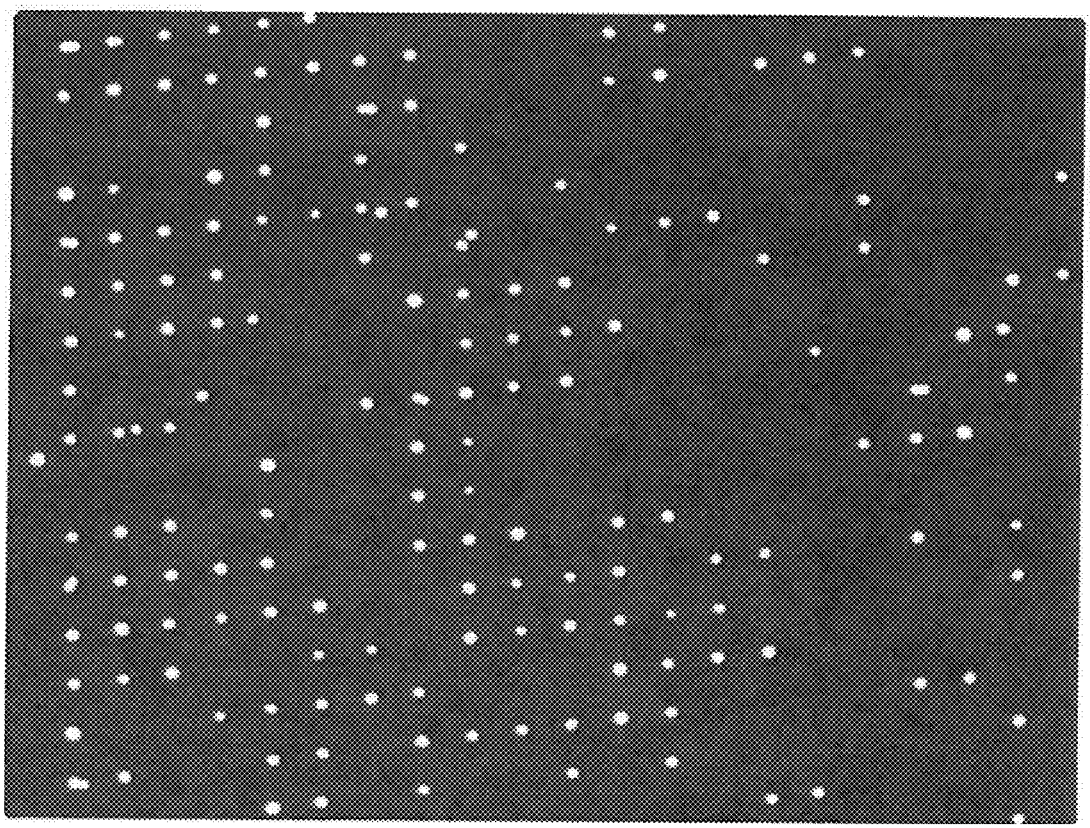
FIG. 6 is a view showing a state of captured cells according to the embodiment of the present invention.
Figure 7:
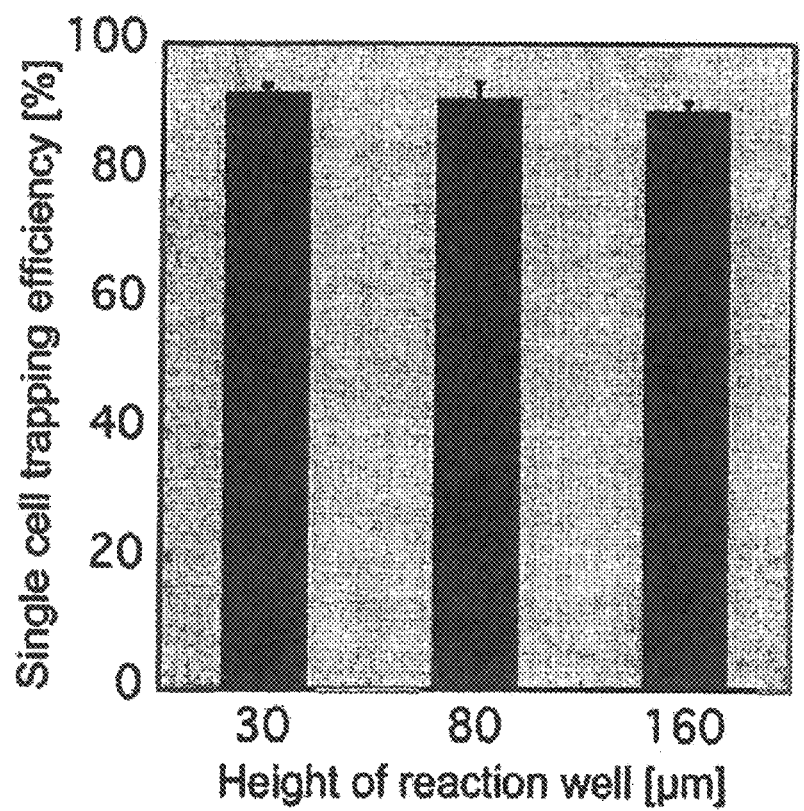
FIG. 7 is a diagram illustrating a relation between the height (μm) of the reaction microchamber and the single cell recovery efficiency (%) according to the embodiment of the present invention.
Figure 8:
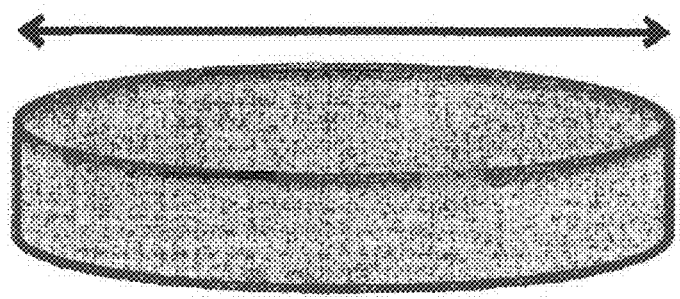
FIG. 8 is a schematic view showing a microchamber with an enlarged diameter.
Figure 10:
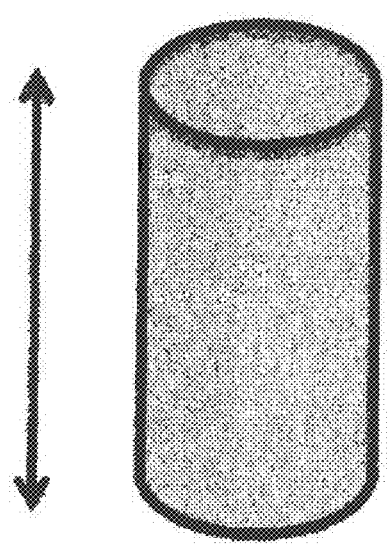
FIG. 10 is a schematic view showing a microchamber with a raised height.
Figure 11:
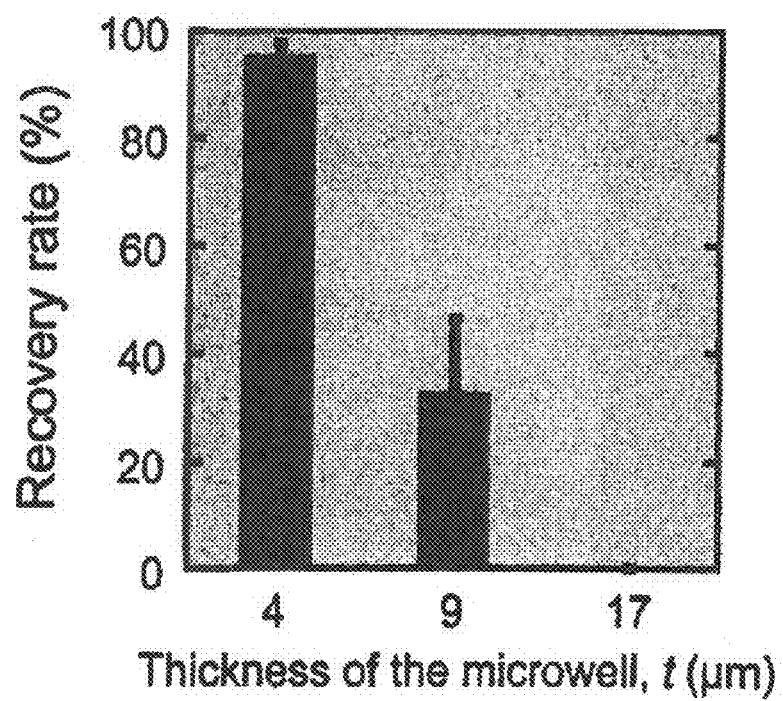
FIG. 11 is a view showing a problem caused by raising a height of microchamber.
Figure 12:
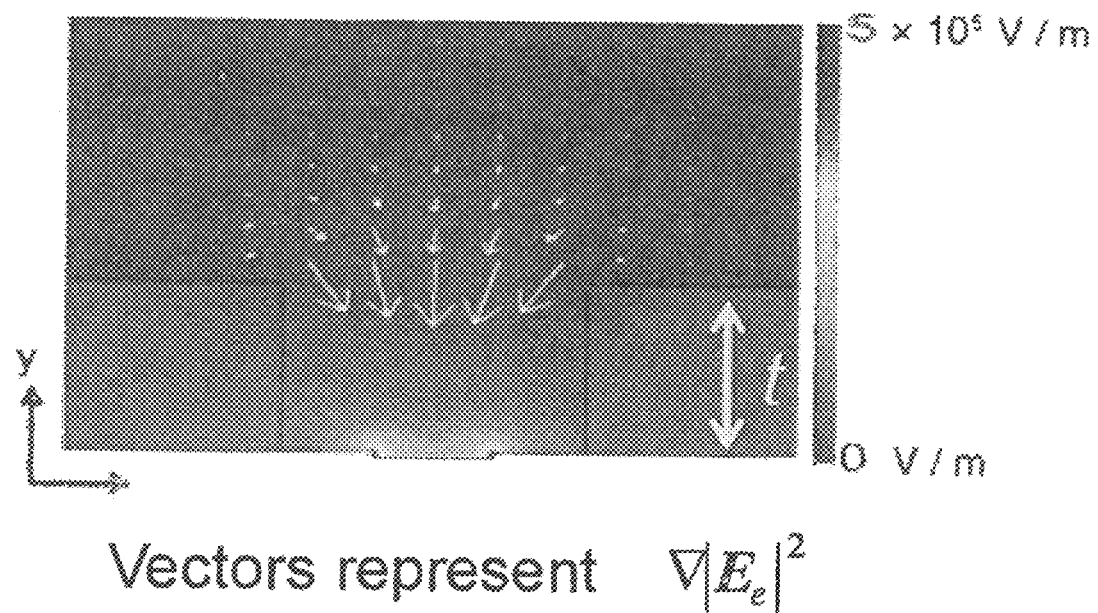
FIG. 12 is a view showing a result of simulating an electric field.

FIG. 4 is a diagram illustrating flow velocities and flow lines in a reaction microchamber 30 µm in height according to the embodiment of the present invention. FIG. 5 is a diagram illustrating flow velocities and flow lines in a reaction microchamber 80 µm in height. In FIGS. 4 & 5, the vertical arms indicate distance (µm) along the X-axes and the horizontal axes indicate distance (µm) along the Y-axes. FIG. 6 is a view showing a state of captured cells according to the embodiment of the present invention. FIG. 7 is a diagram illustrating a relation between the height (µm) of reaction microchamber and the single cell recovery efficiency according to the embodiment of the present invention. In FIG. 7, the vertical axis indicates single cell recovery efficiency (%) and the horizontal axis indicates the height (µm) of reaction microchamber.

As these FIGS. 4-7 illustrate, according to the microchamber array device of the present invention, even when the height of the reaction microchambers are varied, no big variation is observed in the cell recovery efficiency and the high cell recovery efficiency is maintained. Because, in the flow path, the flow is laminar and little turbulent even though the reaction microchambers exist in the upper side of the path so that the flow velocity distribution is little affected. And it is grasped that the single cell capturing is conducted even when the microchambers are enlarged.

The reaction microchamber can be manufactured in diameter of 20 µm-200 µm and in height of 10 µm-1000 µm. The cell recovery efficiency measured with the microchamber array device of the present invention is 92±2%.

In PTL-1, the microchamber is 25-35 µm in diameter, 15 µm in height (depth) and 7.3-14.4 pL in volume, and its recovery of is 10% according to the experimental result as described in NPL-3.

As described above, according to the microchamber array device of the present invention, it is possible to maintain the cell recovery efficiency of 90% or more while to dilute the intracellular substance 1000 times or more with enlarging the volume of the closed microchamber 12.

The maximum number of cells, which C1 (Fluidigm made), a single-cell RT-PCR device available in the market, can simultaneously analyze, is 96 at present. As the microchamber array device of the present invention has a simple structure and is easy of integration, it is able to conduct massively parallel cell analysis. For example, simultaneous analysis of 10000 cells will be realized, because it is possible to form 10000 of reaction microchambers in one square centimeter, which can achieve a high dilution rate. Thus, its applications are expected not only for basic research of grasping the state of heterogeneity of cell but for medical care, such as detection of rare cancer cells.

The present invention is not limited to the above embodiments but may be diversely modified and varied. Thus, the modifications and variations are not excluded from the scope of protection of the present invention.

INDUSTRIAL APPLICABILITY

The present invention is applicable to a microchamber array device having built-in reaction microchambers, in which the dilution rate can be greatly increased at the same time as dramatically raising cell recovery efficiency and a method of analyzing inspection object using same.

The invention claimed is:
1. A microchamber array device, comprising:
a cell capturing microchamber array including a plurality of cell capturing microchambers for capturing cells by dielectrophoresis, the cell capturing microchambers including electrodes and photoresists; and a reaction microchamber array including a plurality of reaction microchambers corresponding to the cell capturing microchambers;

wherein each of the cell capturing microchambers is the same as each of the cells in diameter and is between 0 μm and 9 μm in height, and each of the reaction microchambers is 30 μm 1000 μm in height, wherein the cell capturing microchamber array is set above the reaction microchamber array so that openings in the reaction microchambers face openings in the cell capturing microchambers, wherein the cell capturing microchamber array and reaction microchamber array are configured to be relatively movable from a position in which the cell capturing microchamber array is separated from the reaction microchamber array to a position in which the cell capturing microchamber array contacts the reaction microchamber array to form a plurality of closed microchambers, each of the closed microchambers including one of the cell capturing microchambers and a respective one of the reaction microchambers, wherein, in the position in which the cell capturing microchamber array is separated from the reaction microchamber array, a flow path is formed between the reaction microchambers and the cell capturing microchambers, and wherein, in the position in which the reaction microchamber array contacts the cell capturing microchamber array, the flow path is closed.

2. The microchamber array device according to claim 1, wherein the cells captured by cell capturing microchambers in the closed microchambers are crushable.

3. A method of analyzing inspection object using a microchamber array device according to claim 1, the method comprising:

introducing a cell suspension into the flow path between the reaction microchambers and the cell capturing microchambers;

capturing the cells by di electrophoresis;

exchanging reagents by introducing analysis solution through the flow path;

sealing the captured cells with the cell capturing microchambers and the reaction microchambers by closing the flow path; and analyzing the cells.

4. A method of analyzing inspection object using a microchamber array device according to claim 2, the method comprising:

introducing a cell suspension into the flow path between the reaction microchambers and the cell capturing microchambers;

capturing the cells by di electrophoresis;

exchanging reagents by introducing analysis solution through the flow path;

sealing the captured cells with the cell capturing microchambers and the reaction microchambers by closing the flow path; and analyzing the cells.

* * * * *